Aug. 13, 1940. C. H. PERKINS Plant Pat. 416
ROSE PLANT
Filed Feb. 1, 1940
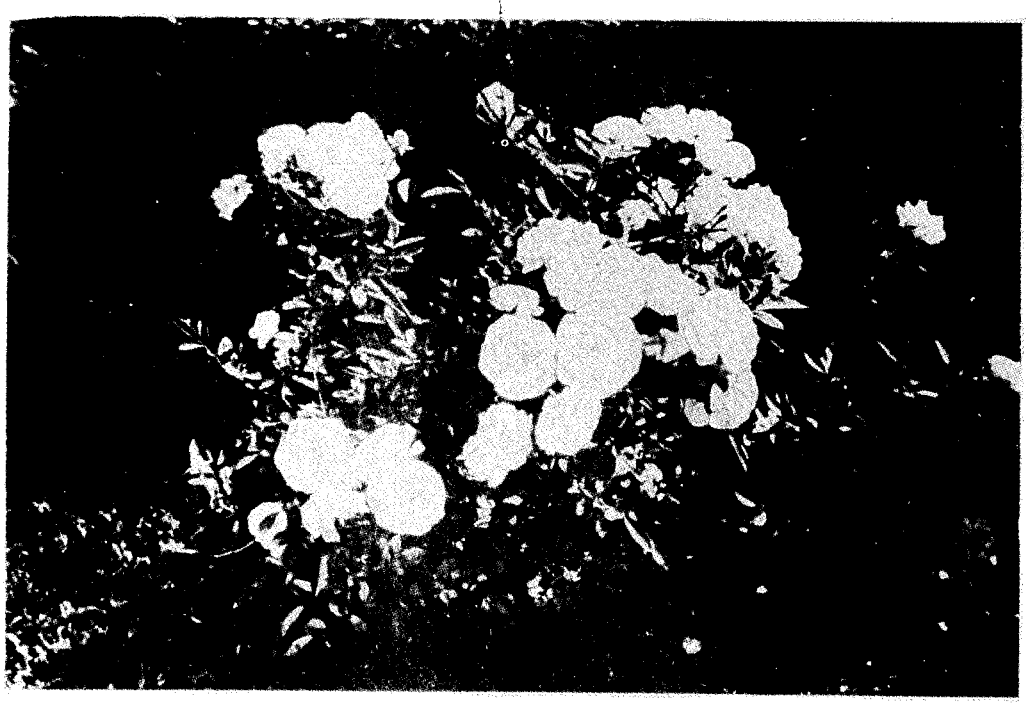
Inventor
C. H. Perkins
By Robert Tobb
Attorneys, Patented Aug. 13, 1940

Plant Pat. 416

UNITED STATES PATENT OFFICE

416

ROSE PLANT

Charles H. Perkins, Newark, N. Y., assignor to Jackson & Perkins Company, Newark, N. Y., a corporation of New York Application February 1, 1940, Serial No. 316,852

1 Claim. (Cl. 47—61)

This invention relates to a new and distinct variety of rose plant of the large flowered polyantha or floribunda group. The new variety originated as a sport of the climbing rose plant disclosed in the co-pending application of Alphonse Couteau, Serial No. 314,550, filed January 18, 1940, now Plant Patent 400.

In general details, my new variety is identical with its parent and is primarily distinguished therefrom, and from other known varieties, by its bush form and medium branching habit of growth of the plant, and the continuously recurrent blooming habit of flowers identical with the large white flowers in large clusters of its parent. Thus, compared with its parent, the new variety may be generally characterized as a dwarf variety.

Asexual reproduction has disclosed that the distinguishing characteristics above referred to come true to form.

The following is a detail description of my new variety, all references to color being in accordance with Ridgway's Color Standard:

Parentage: Sport of variety disclosed in co-pending application of Alphonse Couteau, Serial No. 314,550, filed January 18, 1940, now Plant Patent 400.

Classification:

*Botanic.*—Large flowered polyantha.

*Commercial.*—Floribunda.

*Flower*

(Observations made in the fields and gardens of Jackson & Perkins Company, Newark, New York, in the morning of June 30, 1939.)

Blooming habit: Recurrent—continuous.

Bud:

*Size.*—Small.

*Form.*—Short with flat top. Is not affected by wet or hot weather.

*Color.*—When sepals first divide—Chamois, Plate 30. When petals begin to unfurl—Marguerite Yellow, Plate 30. When half blown: inside of petals—Marguerite Yellow, Plate 30. Reverse of petals—Marguerite Yellow, Plate 30.

*Sepals.*—Serrated and hirsute. Curl back when half blown.

*Calyx.*—*Shape*—apple. *Size*—small. *Aspect*—smooth.

*Peduncle.*—*Length*—medium. *Aspect*—prickly. *Color*—Light Cress Green, Plate 31. *Strength*—stiff.

*Opening.*—Bud opens well. Is not affected by adverse conditions.

Bloom:

*Size.*—Small.

*Average size when fully expanded.*—Three inches.

*Borne.*—In flat clusters.

*Stems.*—Medium length; normal strength.

*Form.*—*When first open*—cupped. *Permanence*—flattens.

*Petalage.*—Double (full but open center). Number of petals under normal conditions—15.

*Color.*—Center of flower—White, Plate 53, with slight tinge of Marguerite Yellow, Plate 30. Outer petals—White, Plate 53, with slight tinge of Marguerite Yellow, Plate 30. Base of petals (aiglet)—Primrose Yellow, Plate 30. Inside of petals—White, Plate 53, with slight tinge of Marguerite Yellow, Plate 30. Reverse of petals—White, Plate 53, with slight tinge of Marguerite Yellow, Plate 30. General tonality from a distance—White.

*Discoloration.*—General tonality at end of first day—White, Plate 53, with Marguerite Yellow, Plate 30. Second day—White, Plate 53. Third day—White, Plate 53.

Petals:

*Texture.*—Thin. Are not affected by wet or hot weather.

*Appearance.*—*Inside*—satiny. *Outside*—shiny.

*Form.*—Scalloped.

*Arrangement.*—Informal (with "rags" in center). Petaloids in center—few.

*Persistence.*—Drop off cleanly.

*Fragrance.*—Slight. *Nature*—tea (average hybrid tea scent).

*Lasting quality.*—*On the plant*—very long. *As cut flower*—fair.

Genital organs:

*Stamens, anthers.*—*Size*—small; many. *Color*—Apricot Yellow, Plate 4. *Arrangement*—regular around styles.

*Stamens, filaments (threads).*—*Length*—medium. *Color*—Martius Yellow, Plate 4.

*Pollen.*—Color—Apricot Yellow, Plate 4.

*Styles.*—Bunched; medium length; thin.

*Stigmas.*—*Color*—Martius Yellow, Plate 4. *Ovaries*—all enclosed in calyx.

Fruit: Variety is sterile with its own pollen.

*Plant*

Form: Bush.

Growth: Medium, branching.

Foliage: Seven leaflets or more.

*Size.*—Small.

*Quantity.*—Normal.

*Color.*—*New foliage*: upper side—Light Elm Green, Plate 17; under side—Light Bice Green, Plate 17. *Old foliage*: upper side—Varley's Green, Plate 18; under side—Rainette Green, Plate 31.

*Shape.*—Lanceolate.

*Texture.*—Upper side—glossy, smooth. Under side—smooth. *Ribs and veins*—light.

*Edge.*—Serrated (saw toothed).

*Serration.*—Single; small.

*Rachis.*—*Color*—Light Cress Green, Plate 31. *Under side*—hooked prickles.

*Stipules.*—Medium length; serrated.

*Disease resistance.*—Only slight tendency to black spot.

Wood:

*New wood.*—*Color*—Bice Green, Plate 17. *Bark*—smooth.

*Old wood.*—*Color*—Cress Green, Plate 31. *Bark*—smooth.

Thorns:

*Thorns.*—Quantity on main stalks from base and on laterals from stalk—few. *Form*—broad base, hooked downward. *Color when young*—Mignonette Green, Plate 31. *Position*—irregular.

*Prickles.*—Quantity on main stalks and on laterals—few. *Color*—Mars Brown, Plate 15.

Having thus described my new variety, what I claim as new and desire to secure by Letters Patent is:

A new and distinct variety of rose plant of the large flowered polyantha group, characterized as to novelty by its similarity in general details to its parent, but distinguishing therefrom in its bush form and medium branching habit of growth of the plant, and the continuously recurrent blooming habit of its flowers, substantially as shown and described.

CHARLES H. PERKINS.